United States Patent
Taylor et al.

(10) Patent No.: US 8,071,829 B2
(45) Date of Patent: Dec. 6, 2011

(54) ALKYLATION PROCESS

(75) Inventors: Bradley M. Taylor, Tulsa, OK (US); Barbara A. Todd, Niotaze, KS (US)

(73) Assignee: ConocoPhillips Company, Houston, TX (US)

( * ) Notice: Subject to any disclaimer, the term of this patent is extended or adjusted under 35 U.S.C. 154(b) by 477 days.

(21) Appl. No.: 12/389,695

(22) Filed: Feb. 20, 2009

(65) Prior Publication Data

US 2010/0217056 A1 Aug. 26, 2010

(51) Int. Cl.
*C07C 2/64* (2006.01)

(52) U.S. Cl. .......... 585/455; 585/447; 585/448; 585/449

(58) Field of Classification Search .................. 585/455, 585/447, 448, 449
See application file for complete search history.

(56) References Cited

U.S. PATENT DOCUMENTS

| 5,082,990 | A  | 1/1992  | Hsieh et al.   |
| 5,347,061 | A  | 9/1994  | Harandi et al. |
| 7,371,910 | B2 | 5/2008  | Yeh et al.     |
| 7,439,411 | B2 | 10/2008 | Canos et al.   |
| 7,449,420 | B2 | 11/2008 | Hwang et al.   |

FOREIGN PATENT DOCUMENTS

CA 2599344 A1 9/2006

*Primary Examiner* — Thuan Dinh Dang

(57) ABSTRACT

A process is disclosed for the alkylation of aromatics by charging a hydrocarbon feed containing aromatic hydrocarbons and olefinic hydrocarbons to a distillation column for separation into at least one fraction; removing an aromatics/olefin stream containing at least a portion of the aromatic hydrocarbons and at least a portion of the olefinic hydrocarbons; charging the aromatics/olefin stream to an alkylation reactor, operated at a temperature in the range of from about 80° C. to about 220° C., for alkylation of at least a portion of the aromatic hydrocarbons with the olefinic hydrocarbons; recycling at least a portion of the resulting reactor effluent to the distillation column; and removing a product stream containing alkylated aromatics from the distillation column.

19 Claims, 11 Drawing Sheets

ALKYLATION PROCESS

FIELD OF THE INVENTION

The present invention relates to a process for the alkylation of aromatic hydrocarbons with olefinic hydrocarbons. In another aspect, this invention relates to a process for the alkylation of aromatic hydrocarbons with olefinic hydrocarbons in a reactive distillation system.

BACKGROUND OF THE INVENTION

Current fuel regulations place limits on the allowable concentration levels of benzene and other light aromatics, and are expected to tighten further in the future. Thus, there is an incentive to convert such light aromatics to heavier diesel range hydrocarbons.

SUMMARY OF THE INVENTION

In accordance with the present invention, a process is provided including the following:
(a) charging a hydrocarbon feed, comprising aromatic hydrocarbons having from six to seven carbon atoms per molecule and olefinic hydrocarbons having from five to six carbon atoms per molecule, to a distillation column for separation into at least one fraction;
(b) removing an aromatics/olefin stream comprising at least a portion of the aromatic hydrocarbons and at least a portion of the olefinic hydrocarbons from the distillation column;
(c) charging the aromatics/olefin stream to an alkylation reactor, operated at a temperature in the range of from about 80° C. to about 220° C., for alkylation of at least a portion of the aromatic hydrocarbons with the olefinic hydrocarbons, thereby resulting in a reactor effluent comprising: 1) reaction products comprising aromatics having from ten to sixteen carbon atoms per molecule, and 2) unreacted hydrocarbons comprising at least a portion of the aromatic hydrocarbons and at least a portion of the olefinic hydrocarbons;
(d) recycling, as a recycle stream, at least a portion of the reactor effluent to the distillation column; and
(e) removing, from the distillation column, a product stream comprising at least a portion of the reaction products.

DETAILED DESCRIPTION OF THE INVENTION

Figure 1:
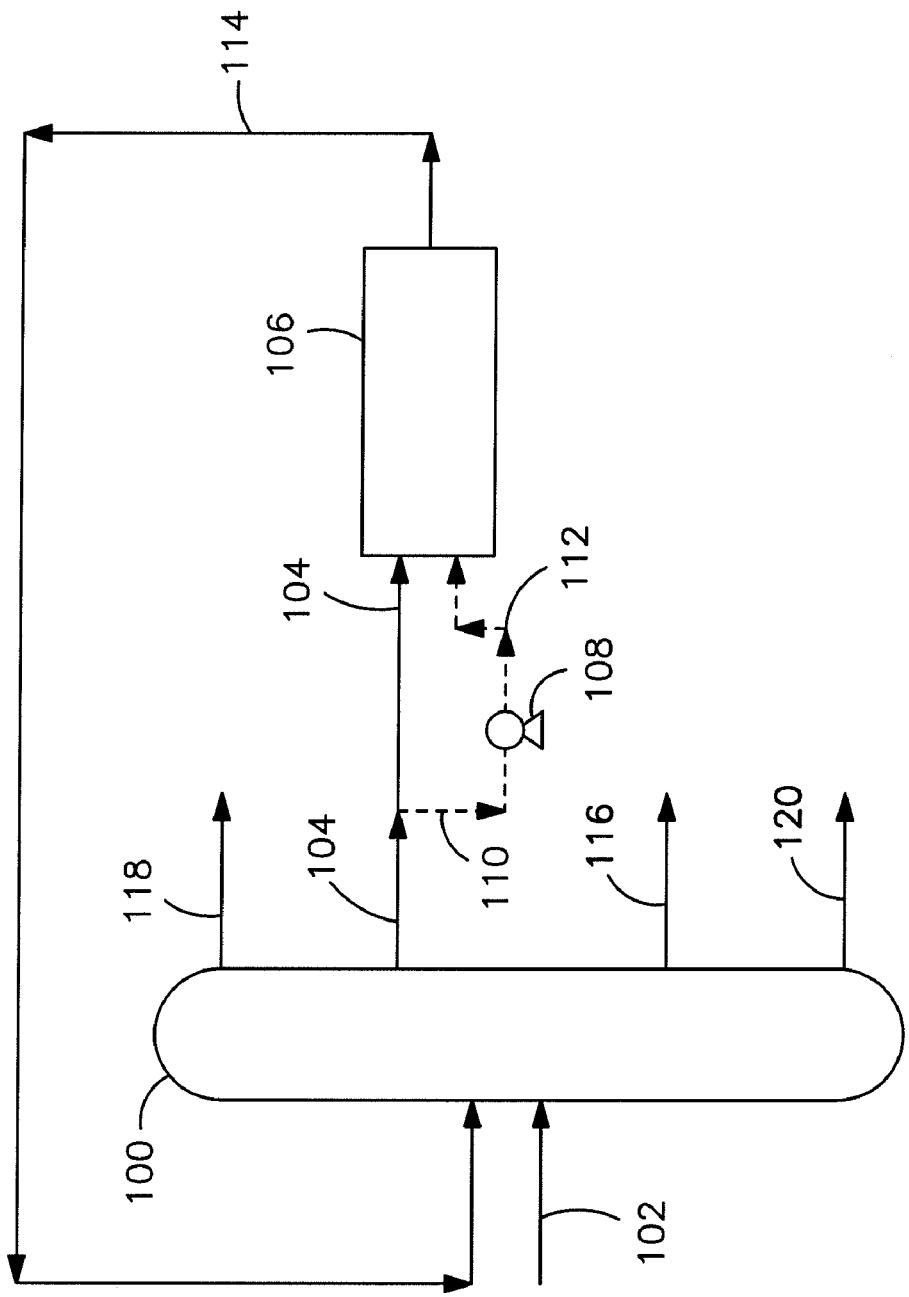
FIG. 1 is a simplified schematic flow diagram presenting an embodiment of the present invention.

The hydrocarbon feed of the present invention can be any group of hydrocarbons comprising, consisting of, or consisting essentially of aromatic hydrocarbons having from six to seven carbon atoms per molecule and olefinic hydrocarbons having from five to six carbon atoms per molecule.

The hydrocarbon feed can also comprise, consist of, or consist essentially of aromatic hydrocarbons having from six to nine carbon atoms per molecule; and olefinic hydrocarbons having from four to seven carbon atoms per molecule.

The hydrocarbon feed can also comprise, consist of, or consist essentially of aromatic hydrocarbons having from six to nine carbon atoms per molecule; olefinic hydrocarbons having from four to seven carbon atoms per molecule, and other hydrocarbons selected from the group consisting of paraffins having from five to twelve carbon atoms per molecule, heavy olefins having from eight to ten carbon atoms per molecule, heavy aromatics having from ten to eleven carbon atoms per molecule, and combinations thereof.

The hydrocarbon feed can also comprise, consist of, or consist essentially of aromatic hydrocarbons having from six to nine carbon atoms per molecule; olefinic hydrocarbons having from four to seven carbon atoms per molecule, and other hydrocarbons selected from the group consisting of paraffins having from four to twelve carbon atoms per molecule, heavy olefins having from eight to twelve carbon atoms per molecule, heavy aromatics having from ten to twelve carbon atoms per molecule, and combinations thereof.

The hydrocarbon feed is charged to a distillation column for separation into at least one fraction. An aromatics/olefin stream comprising at least a portion of the aromatic hydrocarbons and at least a portion of the olefinic hydrocarbons is removed from the distillation column. The aromatics/olefin stream is charged to an alkylation reactor, operated at a temperature in the range of from about 80° C. to about 220° C., for alkylation of at least a portion of the aromatic hydrocarbons with the olefinic hydrocarbons, thereby resulting in a reactor effluent comprising, consisting of, or consisting essentially of: 1) reaction products comprising, consisting of, or consisting essentially of aromatics having from ten to sixteen carbon atoms per molecule, or having from ten to twelve carbon atoms per molecule, and 2) unreacted hydrocarbons comprising, consisting of, or consisting essentially of: at least a portion of the aromatic hydrocarbons and at least a portion of the olefinic hydrocarbons.

At least a portion of the reactor effluent is recycled, as a recycle stream, to the distillation column. The recycle stream is preferably charged to the distillation column at a location above the location the hydrocarbon feed is charged to the distillation column. A product stream comprising, consisting of, or consisting essentially of at least a portion of the reaction products is removed from the distillation column. Preferably, the reaction products are present in the product stream in an amount of at least about 1 vol. %, and more preferably in an amount of at least about 3 vol. %.

A light hydrocarbon stream comprising hydrocarbons having equal to or less than five carbon atoms per molecule is removed from the top portion of the distillation column. Preferably, the light hydrocarbon stream is removed from the distillation column above the location the aromatics/olefin stream is removed from the distillation column.

A heavy hydrocarbon stream comprising hydrocarbons having equal to or greater than seventeen carbon atoms per molecule is removed from the bottom portion of the distillation column. Preferably, the heavy hydrocarbon stream is removed from the distillation column below the location the product stream is removed from the distillation column.

The aromatic hydrocarbons are present in the aromatics/olefin stream in an amount of at least about 5 vol. %, or at least about 20 vol. %.

The olefinic hydrocarbons are present in the aromatics/olefin stream in an amount of at least about 5 vol. %, or at least about 10 vol. %.

The alkylation reactor preferably contains a solid acid catalyst. The solid acid catalyst preferably comprises a zeolite.

The temperature of the alkylation reactor is preferably in the range of from about 100° C. to about 205° C., more preferably from about 160° C. to about 205° C.

Preferably, at least about 3%, and more preferably at least about 10%, of the aromatic hydrocarbons present in the hydrocarbon feed are converted to reaction products.

Preferably, the pressure of said distillation column is in the range of from about 0 to about 650 psig, or from about 10 to about 650 psig; and the pressure of the alkylation reactor is in the range of from about 250 to about 650 psig, or from about 550 to about 650 psig.

Referring to FIG. 1, the hydrocarbon feed is passed to the distillation column 100 by line 102, for separation into at least one fraction. The aromatics/olefin stream is removed from distillation column 100 and charged to alkylation reactor 106 by line 104. Alternatively, the aromatics/olefin stream is passed to a pump 108 by lines 104 and 110, and is passed from pump 108 to the alkylation reactor 106 by line 112. At least a portion of the reactor effluent is removed from the alkylation reactor 106, and charged to distillation column 100, by line 114. The product stream is removed from distillation column 100 by line 116. The light hydrocarbon stream is removed from distillation column 100 by line 118. The heavy hydrocarbon stream is removed from distillation column 100 by line 120.

The following examples are provided to further illustrate this invention and are not to be considered as unduly limiting the scope of this invention.

EXAMPLES

Example I

In eight different runs, an aromatic/olefin hydrocarbon feed was passed over a Beta zeolite catalyst (1/16-inch extrudates) at a feed rate of about 45 ml/hr for the alkylation of the aromatics with the olefins. The zeolite catalyst was mixed with silica beads resulting in a total volume of about 25 ml. Fresh catalyst was used for each Run. The aromatic/olefin hydrocarbon feed was a mixture simulating a benzene and olefin rich stream leaving an FCC naphtha fractionation column containing 1 wt % benzene, 50 wt % n-hexane, 20 wt % 1-hexene, and 29 wt % toluene. The temperatures, pressures, LHSV's, zeolite catalyst quantities, and conversion results for each of Runs 1-8 are presented in Table 1 below.

TABLE 1

| Run | Temp. (° C.) | Pressure (psig) | LHSV ($hr^{-1}$) | Zeolite Weight (g) | Benzene Conv. (%) | Toluene Conv. (%) | hexenes Conv. (%) | $C_{11}$-$C_{13}$ Mol % in Effluent |
|---|---|---|---|---|---|---|---|---|
| 1 | 200 | 300 | 2 | 15 | 65.13 | 51.59 | 100.0 | 10.61 |
| 2 | 125 | 300 | 10 | 3 | 5.8 | 9.49 | 37.36 | 3.38 |
| 3 | 125 | 450 | 6 | 5 | 24.5 | 19.28 | 53.5 | 7.37 |
| 4 | 125 | 600 | 2 | 15 | 71 | 60.17 | 99.95 | 10.23 |
| 5 | 200 | 600 | 10 | 3 | 36.45 | 31.09 | 78.06 | 6.77 |
| 6 | 125 | 450 | 6 | 5 | 9.35 | 10.98 | 47.89 | 3.82 |
| 7 | 162.5 | 450 | 6 | 5 | 38.78 | 31.66 | 77.82 | 7.85 |
| 8 | 87.5 | 450 | 6 | 5 | 11.99 | 10.76 | 34.72 | 2.75 |

As can be seen in Table 1, benzene and toluene are effectively alkylated by 1-hexene over a zeolite catalyst at moderate temperatures.

Example II

In five different runs, an aromatic/olefin hydrocarbon feed was passed over 6 gram quantities of a Beta zeolite catalyst (1/16-inch extrudates) at a feed rate of about 60 ml/hr (a LHSV of 6.5 $hr^{-1}$) for the alkylation of the aromatics with the olefins. The zeolite catalyst was mixed with silica beads resulting in a total volume of about 25 ml, and fresh catalyst was used for each Run. The pressure for each Run was 300 psig. The aromatic/olefin hydrocarbon feed concentrations, temperatures, and conversion and yield results (Initial and End of Run) for each of Runs 1-5 are presented in Tables 2 and 3 below.

TABLE 2

| | | Initial | | | |
|---|---|---|---|---|---|
| Run | Temp. (° C.) | Benzene Conv. (%) | 1-Hexene Conv. (%) | Mixed Phenylhexane Selectivity (%) | Mixed Phenylhexane Yield (%) |
| 1* | 250 | 39.5 | 99.7 | | |
| 2* | 300 | 9.5 | 100 | | |
| 3* | 200 | 49.2 | 100 | | |
| 4* | 150 | 57.1 | 99.7 | 33.7 | 18.9 |
| 5† | 200 | 62.3 | 98.8 | 6.13 | 3.82 |

*Feed: 5 wt-% benzene, 5 wt-% 1-hexene, 90 wt-% n-hexane.
†Feed: 5 wt-% benzene, 10 wt-% 1-hexene, 85 wt-% n-hexane

TABLE 3

| | | End of Run (5 hrs. on stream) | | | |
|---|---|---|---|---|---|
| Run | Temp. (° C.) | Benzene Conv. (%) | 1-Hexene Conv. (%) | Mixed Phenylhexane Selectivity (%) | Mixed Phenylhexane Yield (%) |
| 1* | 250 | 22.9 | 97.8 | | |
| 2* | 300 | 2.1 | 97.3 | | |
| 3* | 200 | 44.6 | 98.6 | | |
| 4* | 150 | 24.4 | 95.6 | 92.7 | 22.6 |
| 5† | 200 | 55.8 | 97.9 | 37.5 | 20.9 |

*Feed: 5 wt-% benzene, 5 wt-% 1-hexene, 90 wt-% n-hexane.
†Feed: 5 wt-% benzene, 10 wt-% 1-hexene, 85 wt-% n-hexane As can be seen in the Table 2, the selectivity to monoalkylated phenylhexanes increased after five hours on stream as compared to the initial yields. Also, increasing the 1-hexene/benzene ratio in the feed increased the benzene conversion.

Example III

In each of nine different runs, one of the four hydrocarbon feeds described in Table 4 below was passed over a Beta zeolite catalyst (1/16-inch extrudates) at a feed rate of about 45 ml/hr for the alkylation of the aromatics with the olefins. The zeolite catalyst was mixed with silica beads resulting in a total volume of about 25 ml, and fresh catalyst was used for each Run. The temperatures, pressures, and LHSV's for each of Runs 1-9 are presented in Table 5 below. Conversion and yield data for Runs 1-9 are separately presented in FIGS. 2-10, respectively. FIG. 11 is a plot of benzene conversion (BBL of benzene converted/1000 lbs catalyst/hr) vs. time on stream using the data from Runs 3, 7 and 8.

TABLE 4

| | Full Range FCC Naphtha | 1st Light FCC Naphtha | 2nd Light FCC Naphtha* BP < 120° C. | 3rd Light FCC Naphtha† BP > 120° C. |
|---|---|---|---|---|
| Benzene (wt-%) | 1.029 | 0.529 | 0.784 | 0.008 |
| Olefins (wt-%) | 17.315 | 20.359 | 28.423 | 2.253 |
| Aromatics (wt-%) | 35.572 | 25.129 | 8.240 | 58.069 |
| Sulfur (ppm) | 49 | 2.9 | 2.5 | 6.8 |
| Nitrogen (ppm) | 48 | 29 | 3 | 88 |
| Calculated API (at 15.5° C.) | 50 | 62 | 73 | 37 |
| Wt-% BP > 165° C. | 13 | 8.5 | 0.5 | 24 |

*The 2nd Light FCC Naphtha is that portion of the 1st Light FCC Naphtha boiling at or below 120° C.
†The 3rd Light FCC Naphtha is that portion of the 1st Light FCC Naphtha boiling above 120° C.

TABLE 5

| Run | Feed | Temperature (° C.) | Pressure (psig) | LHSV (hr.$^{-1}$) |
|---|---|---|---|---|
| 1 | Full Range FCC Naphtha | 200 | 600 | 2 |
| 2 | Full Range FCC Naphtha | 200 | 300 | 2 |
| 3 | Full Range FCC Naphtha | 125 | 600 | 2 |
| 4 | 1st Light FCC Naphtha | 85 | 600 | 2 |
| 5 | 1st Light FCC Naphtha | 85 | 600 | 0.67 |
| 6 | 1st Light FCC Naphtha | 200 | 600 | 0.67 |
| 7 | 1st Light FCC Naphtha | 125 | 600 | 2 |
| 8 | 2nd Light FCC Naphtha | 125 | 600 | 2 |
| 9 | 3rd Light FCC Naphtha | 125 | 600 | 2 |

Figure 2:
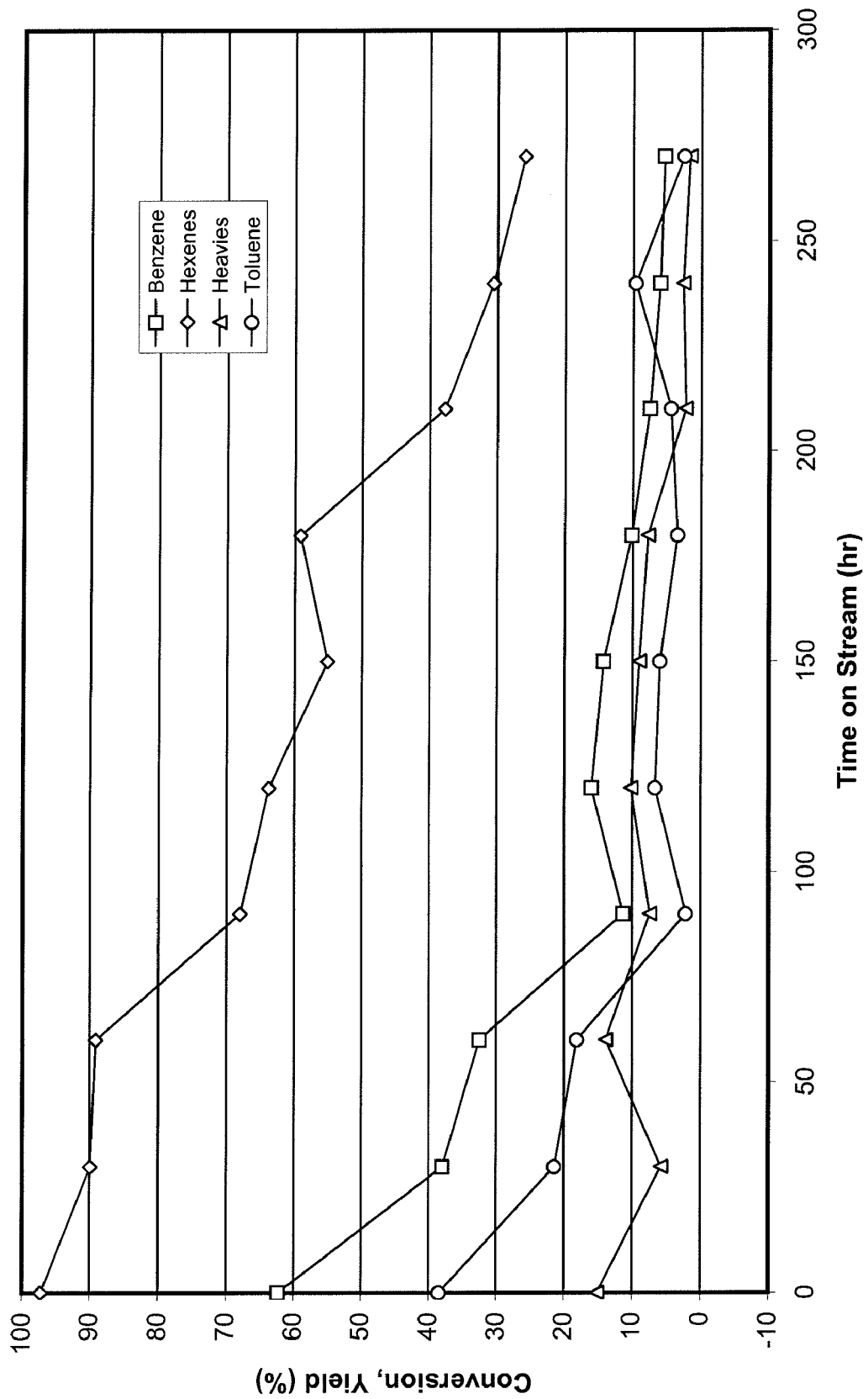
FIG. 2 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 3:
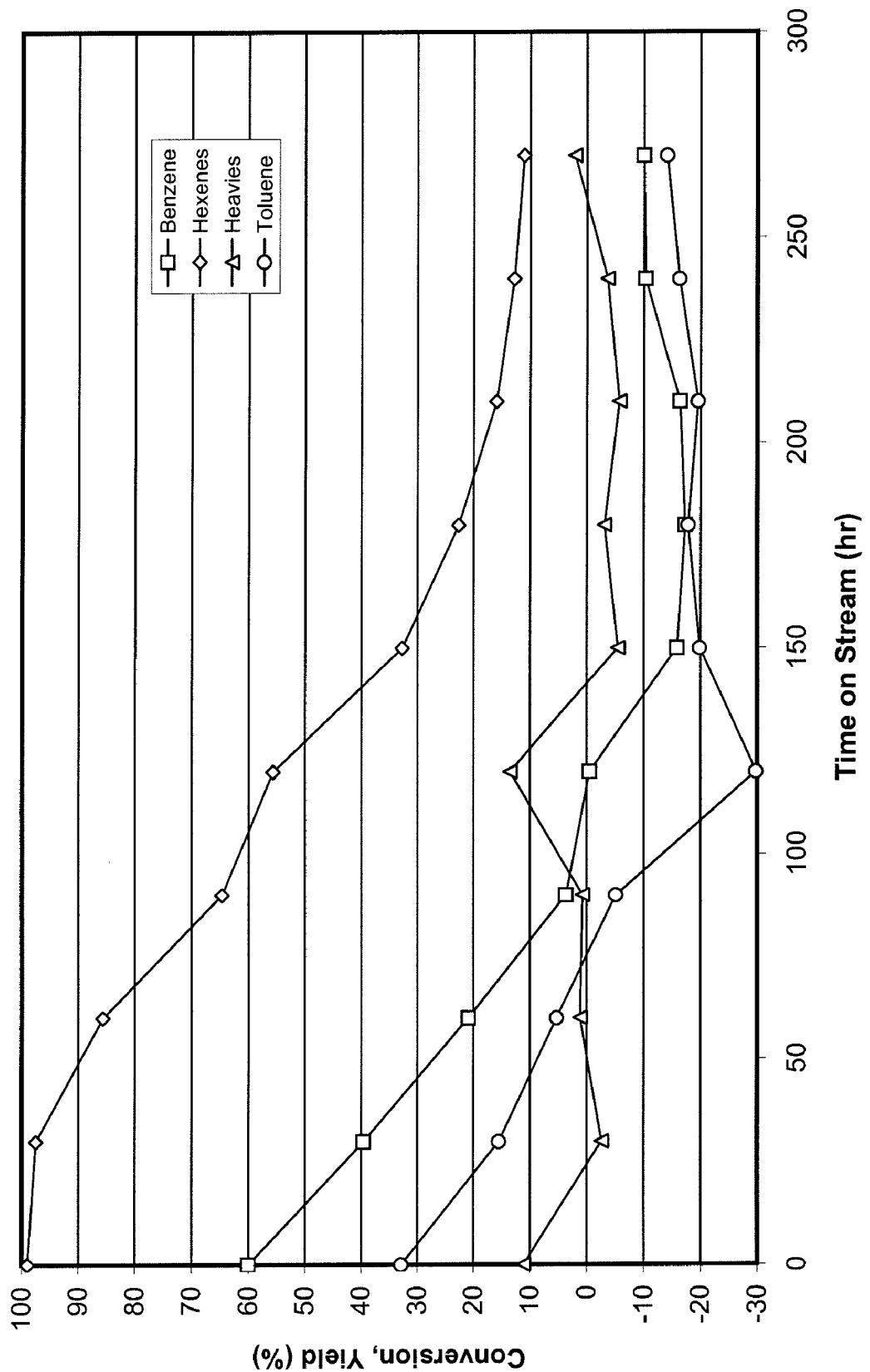
FIG. 3 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 4:
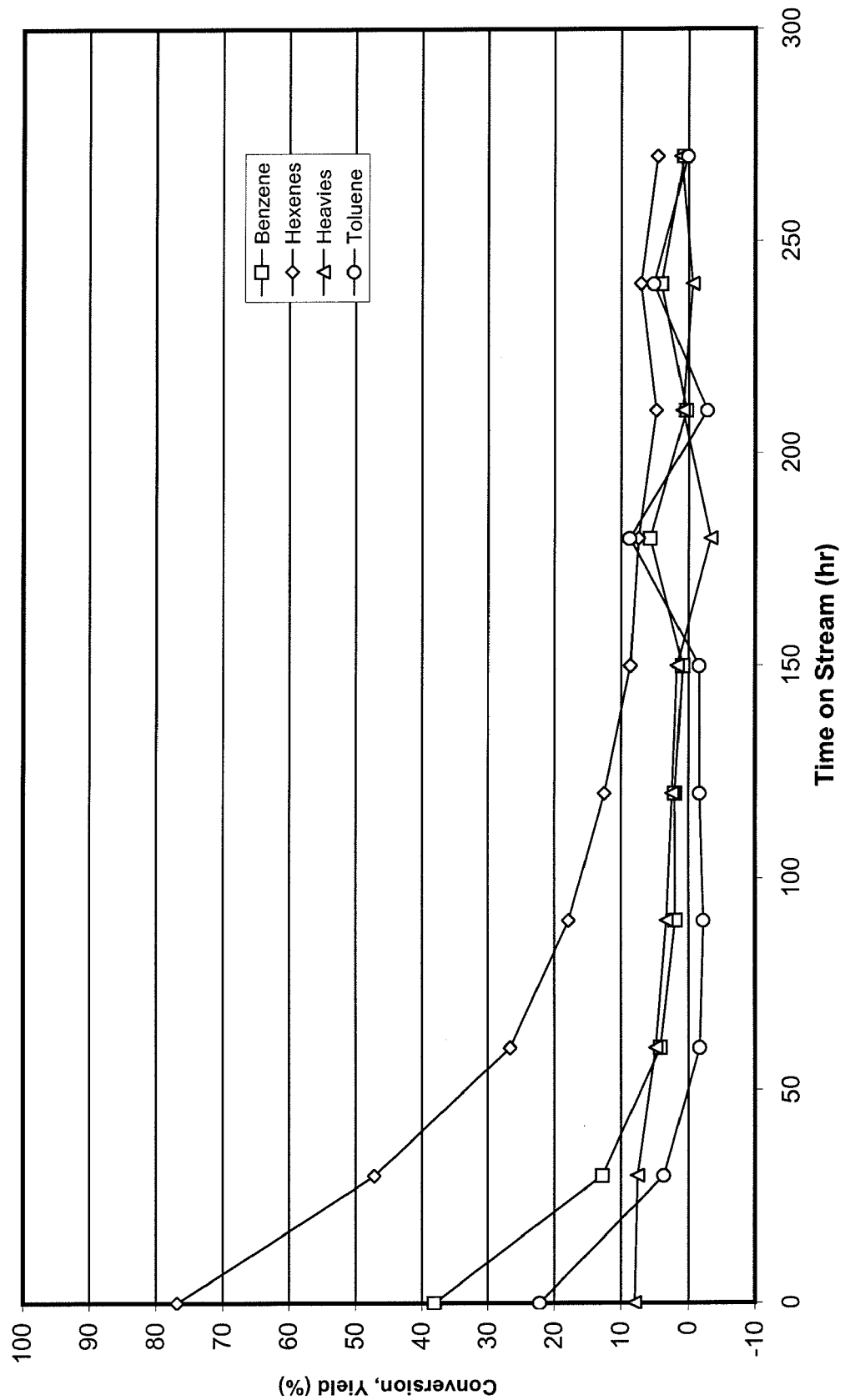
FIG. 4 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 5:
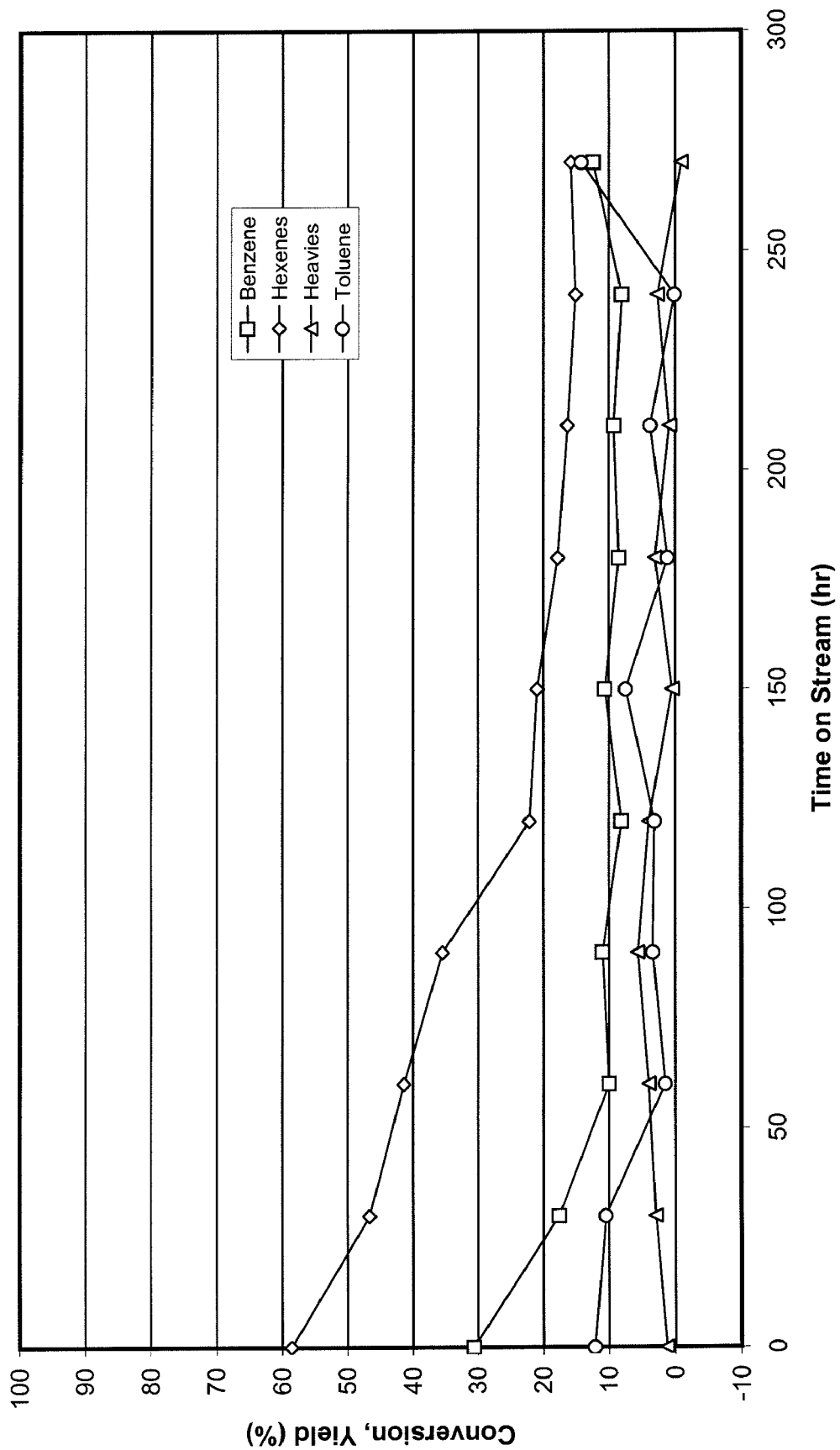
FIG. 5 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 6:
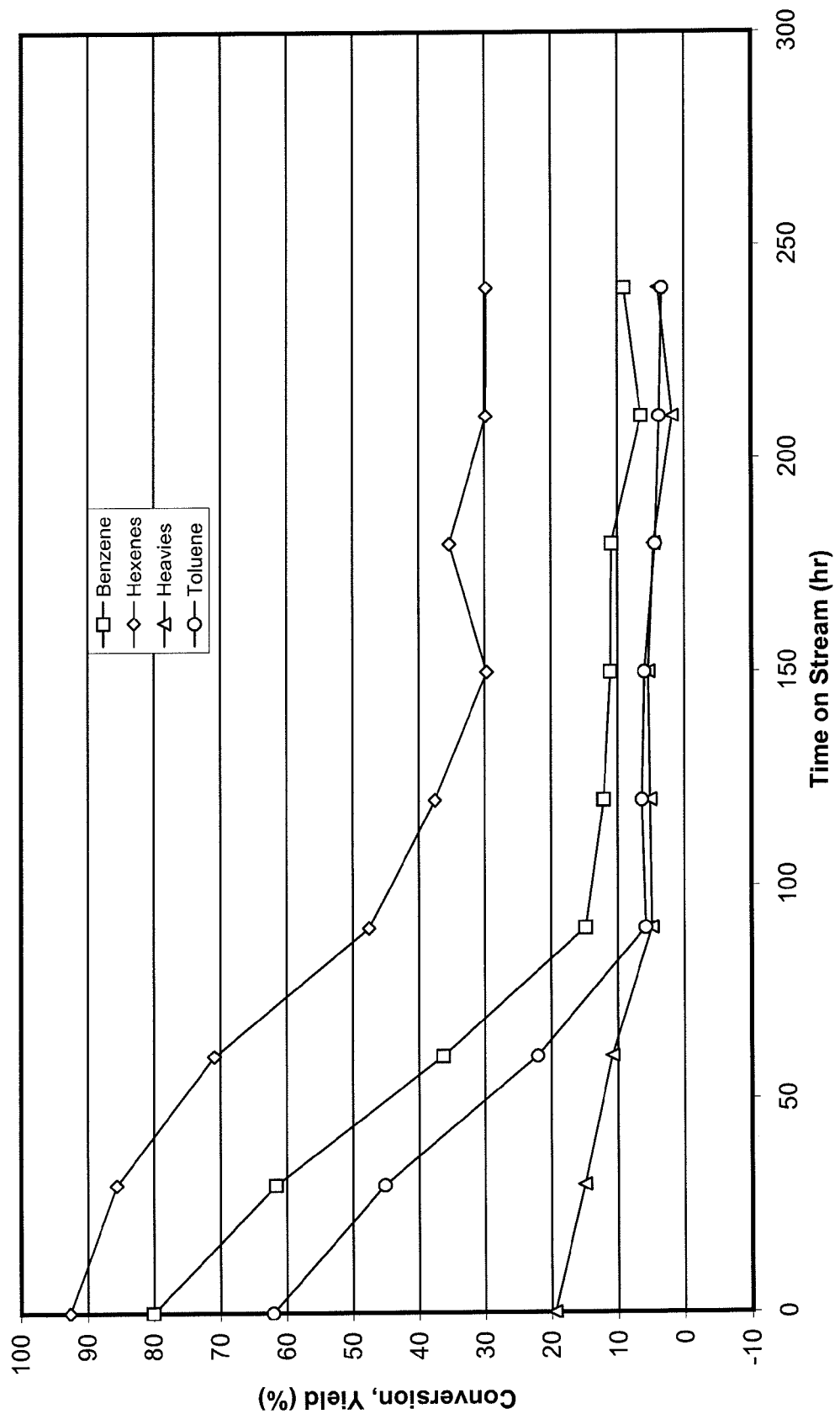
FIG. 6 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 7:
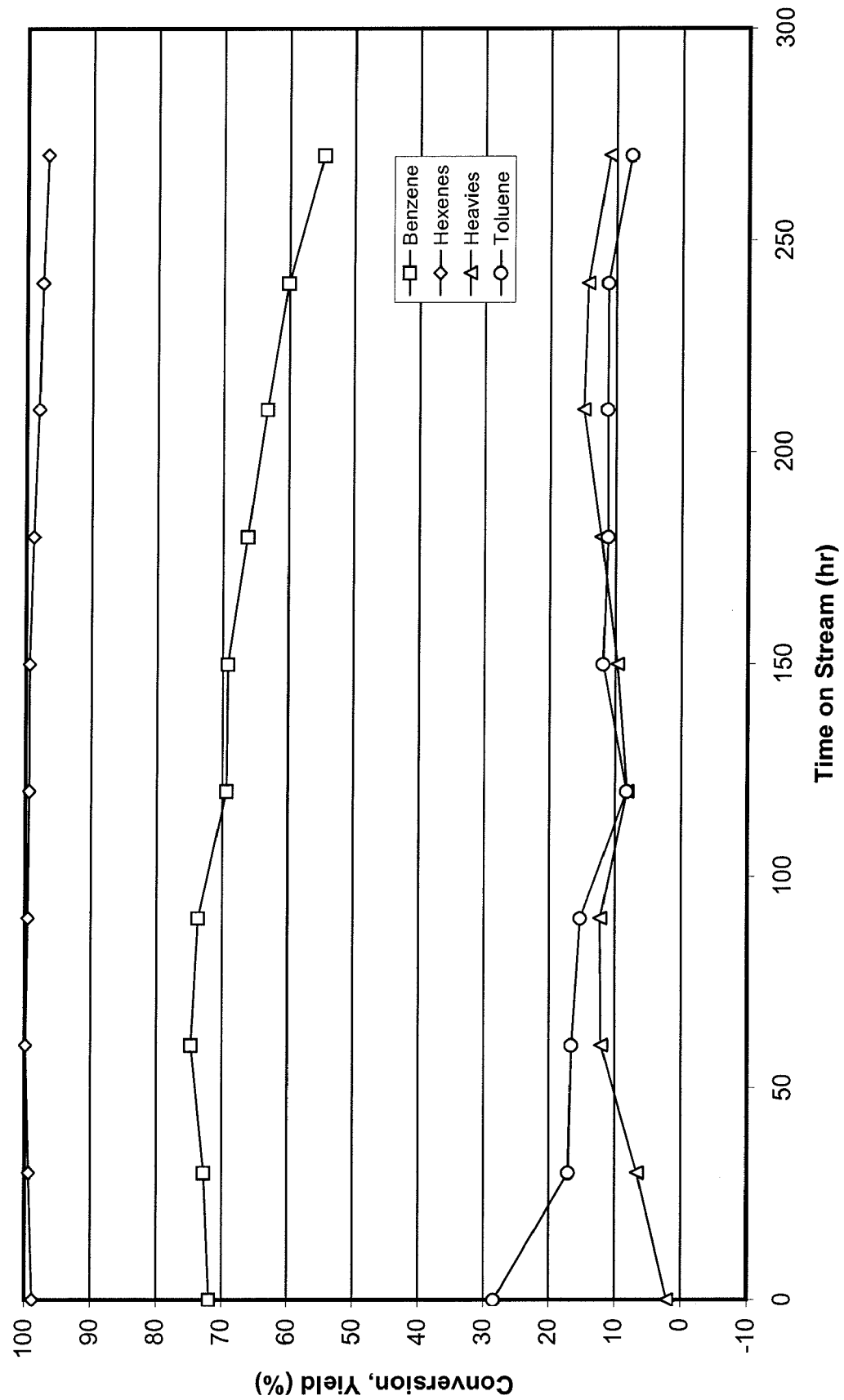
FIG. 7 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.
Figure 8:
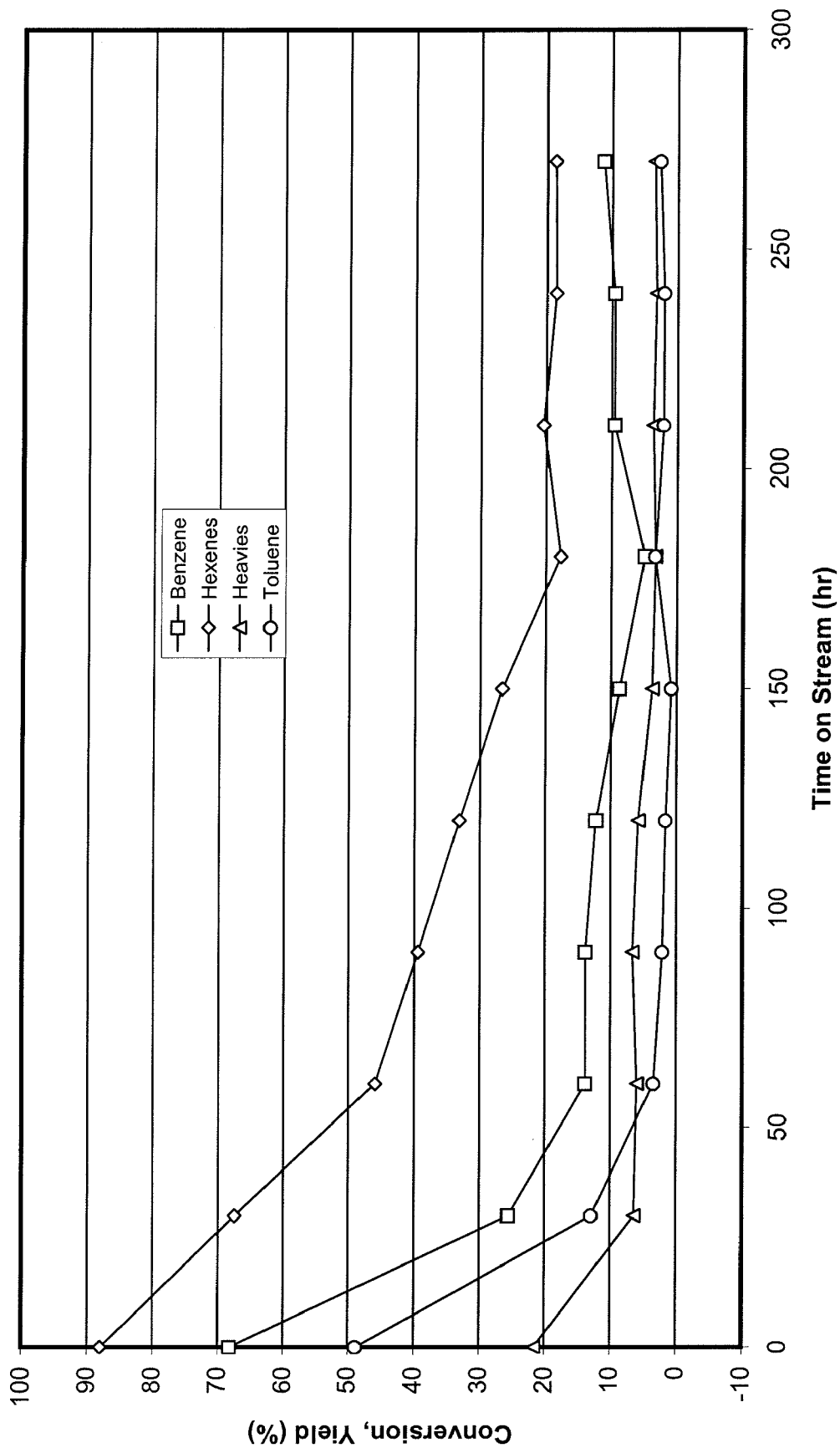
FIG. 8 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.

Comparing the data presented in FIGS. 2-4 (Full Range FCC Naphtha) with that of FIGS. 5-8 (1st Light FCC Naphtha), the end of run benzene conversion for the Full Range FCC Naphtha Runs ranged from about −10% to 6%, while the end of run benzene conversion for the 1st Light FCC Naphtha Runs was much higher, ranging from about 9% to about 55%. Also, the end of run toluene conversion for the Full Range FCC Naphtha Runs ranged from about −14% to about 3%, while the end of run toluene conversion for the 1st Light FCC Naphtha Runs was much higher, ranging from about 3% to about 14%. This demonstrates that alkylation of the lighter fraction of the FCC Naphtha results in higher benzene and toluene conversion than the alkylation of a full range FCC Naphtha (which actually resulted in the production of benzene and toluene in Run 2).

Figure 9:
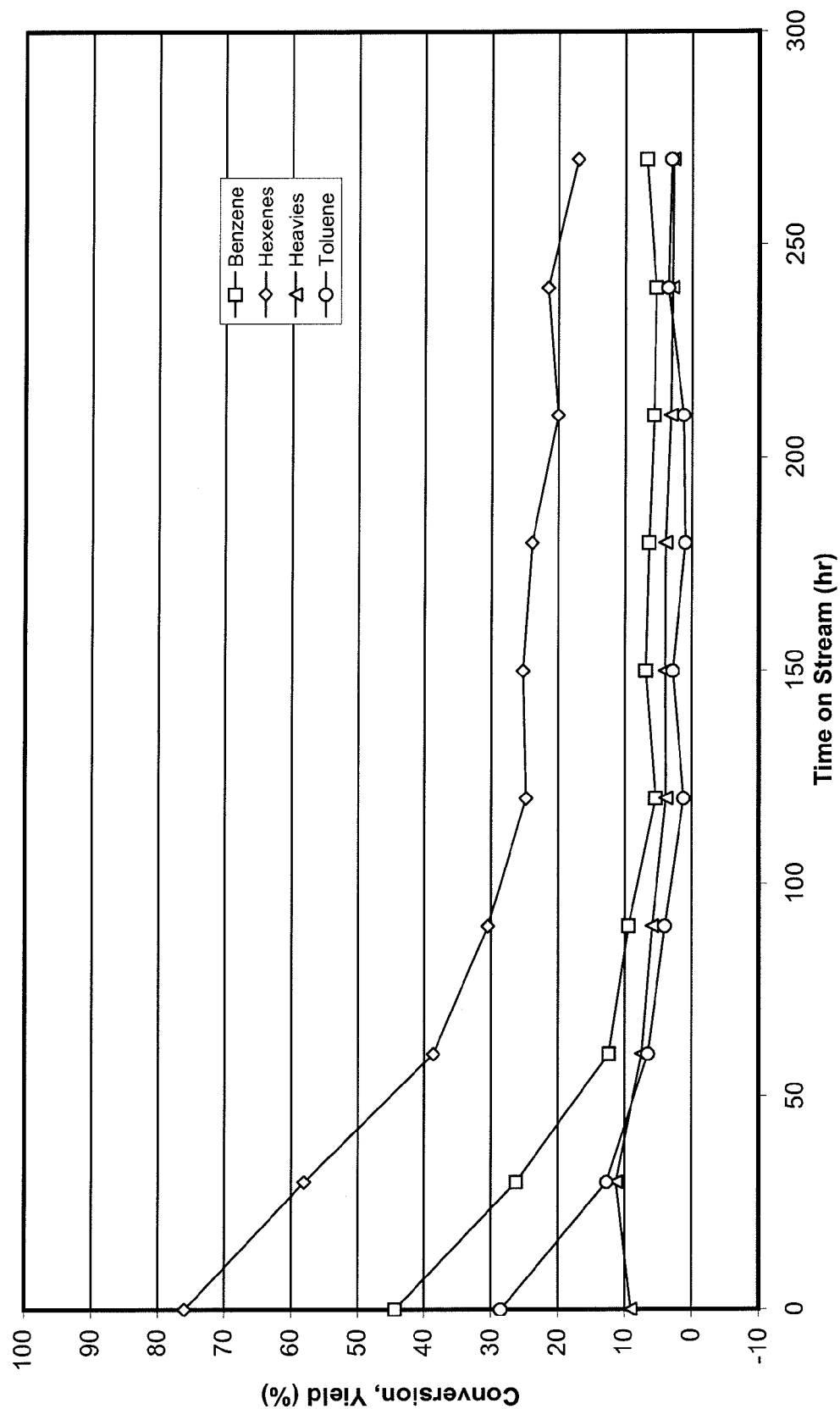
FIG. 9 is a graphic illustration of benzene, toluene and hexenes conversion and of heavies yield vs. Time on Stream data for a run wherein a zeolite catalyst was used to alkylate aromatics within FCC Naphtha with FCC Naphtha olefins.

FIG. 9 also shows that alkylation of a light FCC Naphtha fraction results in higher benzene and toluene conversion than the alkylation of a full range FCC Naphtha.

Figure 10:
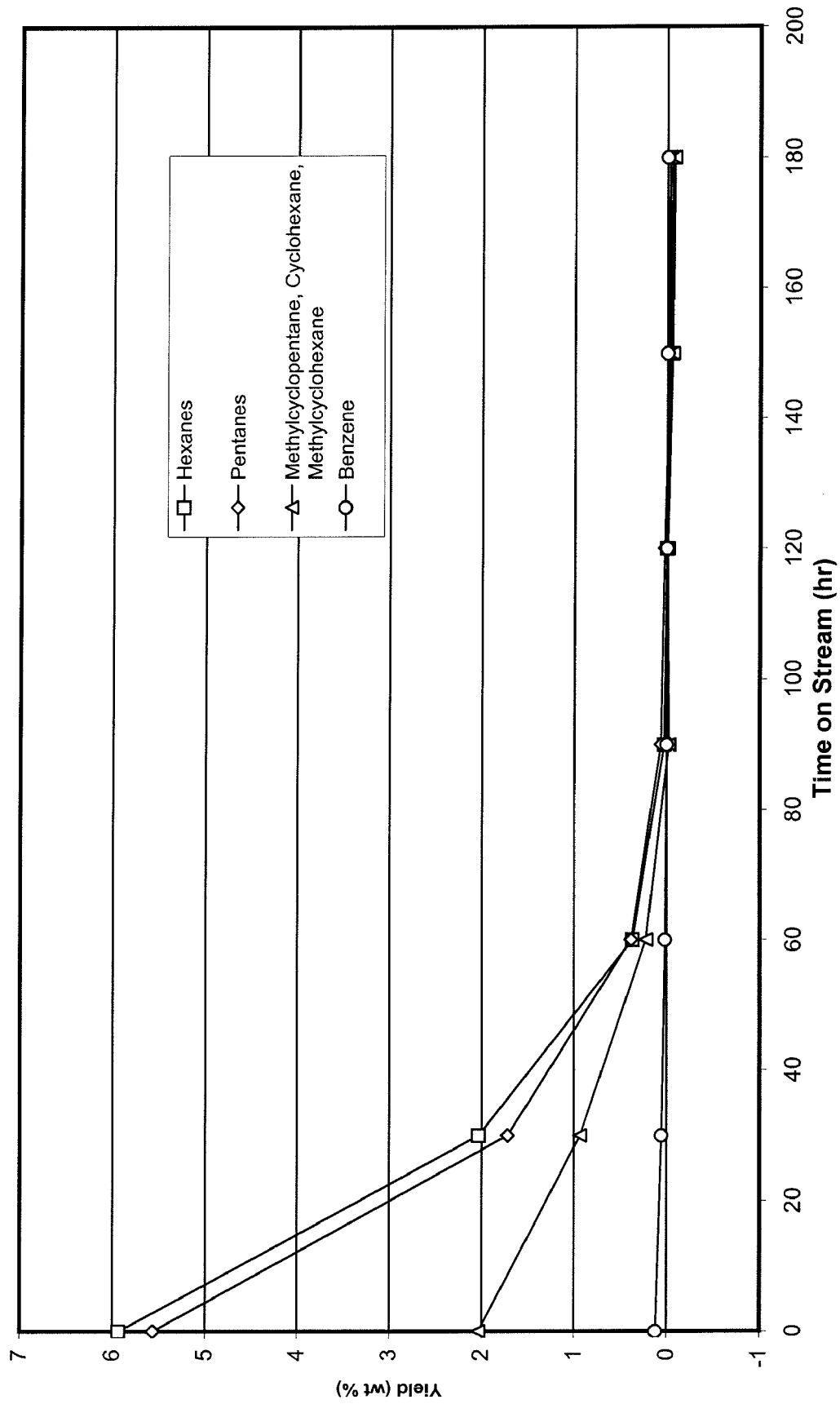
FIG. 10 is a graphic illustration of the pentanes, hexanes, benzene, and combined methylcyclohexane, cyclohexane, and methylcyclopentane yields vs. Time on Stream data for a run wherein a hydrocarbon feed was contacted with a zeolite catalyst at alkylation conditions.
Figure 11:
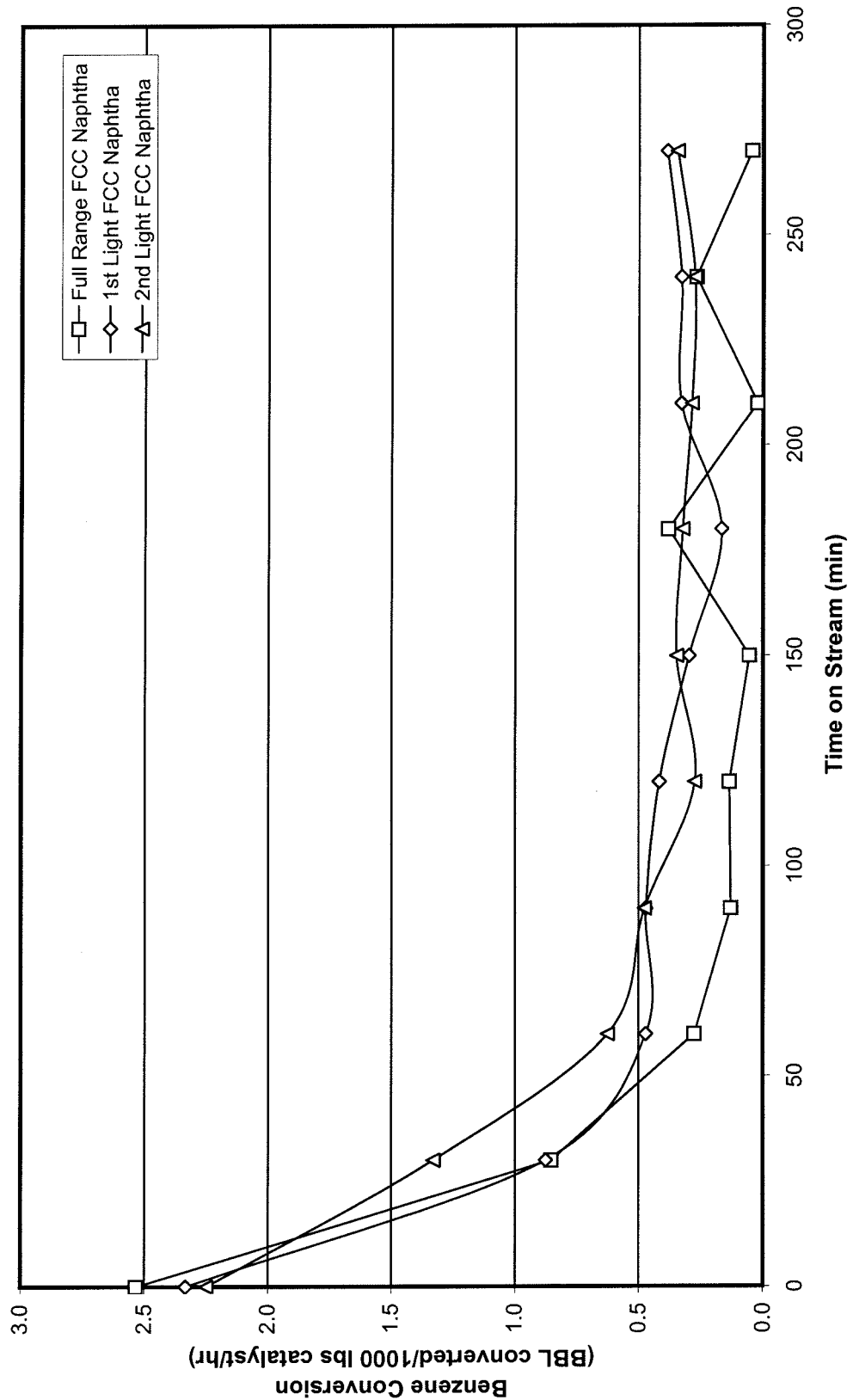
FIG. 11 is a graphic illustration of normalized benzene conversion vs. Time on Stream data for several runs comparing three different hydrocarbon feeds wherein a zeolite catalyst was used to alkylate aromatics within FCC Naphtha with FCC Naphtha olefins.

FIG. 10 shows that subjecting the heavy fraction (boiling above 120° C.) of the Light FCC Naphtha to the zeolite catalyst at benzene alkylation conditions results in the cracking of heavy compounds resulting in catalyst deactivation.

FIG. 11 shows that lighter FCC fractions generally result in higher benzene conversion as compared to heavier FCC Naphtha fractions.

While this invention has been described in detail for the purpose of illustration, it should not be construed as limited thereby but intended to cover all changes and modifications within the spirit and scope thereof.

That which is claimed:

1. A process for alkylating aromatics comprising:
   (a) charging a hydrocarbon feed, comprising aromatic hydrocarbons having from six to seven carbon atoms per molecule and olefinic hydrocarbons having from five to six carbon atoms per molecule, to a distillation column for separation into at least one fraction;
   (b) removing an aromatics/olefin stream comprising at least a portion of said aromatic hydrocarbons and at least a portion of said olefinic hydrocarbons from said distillation column;
   (c) charging said aromatics/olefin stream to an alkylation reactor, operated at a temperature in the range of from about 80° C. to about 220° C., for alkylation of at least a portion of said aromatic hydrocarbons with said olefinic hydrocarbons, thereby resulting in a reactor effluent comprising: 1) reaction products comprising aromatics having from ten to sixteen carbon atoms per molecule, and 2) unreacted hydrocarbons comprising at least a portion of said aromatic hydrocarbons and at least a portion of said olefinic hydrocarbons;
   (d) recycling, as a recycle stream, at least a portion of said reactor effluent to said distillation column; and
   (e) removing, from said distillation column, a product stream comprising at least a portion of said reaction products.

2. A process in accordance with claim 1 wherein said recycle stream is charged to said distillation column at a location above the location said hydrocarbon feed is charged to said distillation column.

3. A process in accordance with claim 1 wherein said hydrocarbon feed is further characterized to comprise hydrocarbons selected from the group consisting of paraffins having from five to twelve carbon atoms per molecule, heavy olefins having from eight to ten carbon atoms per molecule, heavy aromatics having from ten to eleven carbon atoms per molecule, and combinations thereof.

4. A process in accordance with claim 1 wherein said hydrocarbon feed is further characterized to comprise hydrocarbons selected from the group consisting of paraffins having from four to twelve carbon atoms per molecule, heavy olefins having from eight to twelve carbon atoms per molecule, heavy aromatics having from ten to twelve carbon atoms per molecule, and combinations thereof.

5. A process in accordance with claim 4 wherein a light hydrocarbon stream comprising hydrocarbons having equal to or less than five carbon atoms per molecule is removed from the top portion of said distillation column; and wherein a heavy hydrocarbon stream comprising hydrocarbons having equal to or greater than seventeen carbon atoms per molecule is removed from the bottom portion of said distillation column.

6. A process in accordance with claim 5 wherein said light hydrocarbon stream is removed from said distillation column above the location said aromatics/olefin stream is removed from said distillation column; and wherein said heavy hydrocarbon stream is removed from said distillation column below the location said product stream is removed from said distillation column.

7. A process in accordance with claim 1 wherein said aromatic hydrocarbons are present in said aromatics/olefin stream in an amount of at least about 5 vol. %, and wherein said olefinic hydrocarbons are present in said aromatics/olefin stream in an amount of at least about 5 vol. %.

8. A process in accordance with claim 1 wherein said aromatic hydrocarbons are present in said aromatics/olefin stream in an amount of at least about 20 vol. %, and wherein said olefinic hydrocarbons are present in said aromatics/olefin stream in an amount of at least about 10 vol. %.

9. A process in accordance with claim 1 wherein said alkylation reactor contains a solid acid catalyst.

10. A process in accordance with claim 9 wherein said solid acid catalyst comprises a zeolite.

11. A process in accordance with claim 1 wherein said temperature of said alkylation reactor is in the range of from about 100° C. to about 205° C.

12. A process in accordance with claim 1 wherein said temperature of said alkylation reactor is in the range of from about 160° C. to about 205° C.

13. A process in accordance with claim 1 wherein said reaction products comprise aromatics having from ten to twelve carbon atoms per molecule.

14. A process in accordance with claim 1 wherein said reaction products are present in said product stream in an amount of at least about 1 vol. %.

15. A process in accordance with claim 1 wherein said reaction products are present in said product stream in an amount of at least about 3 vol. %.

16. A process in accordance with claim 1 wherein at least about 10% of said aromatic hydrocarbons present in said hydrocarbon feed are converted to reaction products.

17. A process in accordance with claim 1 wherein at least about 3% of said aromatic hydrocarbons present in said hydrocarbon feed are converted to reaction products.

18. A process in accordance with claim 1 wherein the pressure of said distillation column is in the range of from about 0 to about 650 psig; and the pressure of said alkylation reactor is in the range of from about 250 to about 650 psig.

19. A process in accordance with claim 1 wherein the pressure of said distillation column is in the range of from about 10 to about 650 psig; and the pressure of said alkylation reactor is in the range of from about 550 to about 650 psig.

* * * * *